United States Patent
Holtz

(10) Patent No.: US 6,841,523 B1
(45) Date of Patent: Jan. 11, 2005

(54) NAIL POLISH REMOVER

(75) Inventor: Benjamin J. Holtz, St. Louis, MO (US)

(73) Assignee: Vi-Jon Laboratories, Inc., St. Louis, MO (US)

( * ) Notice: Subject to any disclaimer, the term of this patent is extended or adjusted under 35 U.S.C. 154(b) by 0 days.

(21) Appl. No.: 10/670,407

(22) Filed: Sep. 25, 2003

(51) Int. Cl.$^7$ ................................................ A61K 7/00
(52) U.S. Cl. ........................ 510/118; 510/477; 510/505; 510/506
(58) Field of Search ................................ 510/118, 477, 510/505, 506

(56) References Cited

U.S. PATENT DOCUMENTS

| | | |
|---|---|---|
| 2,211,129 A | 8/1940 | Klinkenstein |
| 2,268,642 A | 1/1942 | Carter |
| 4,197,212 A | 4/1980 | Minton et al. |
| 4,485,037 A | 11/1984 | Curtis |
| 4,543,206 A | 9/1985 | Adams |
| 4,594,111 A | 6/1986 | Coonan |
| 4,801,331 A | 1/1989 | Murase |
| 4,824,662 A | 4/1989 | Hofmann |
| 4,867,800 A | 9/1989 | Dishart et al. |
| 5,007,969 A | 4/1991 | Doscher |
| 5,077,038 A | 12/1991 | Hofmann |
| 5,098,594 A | 3/1992 | Doscher |
| 5,173,288 A | 12/1992 | Everhart et al. |
| 5,204,026 A | 4/1993 | Doscher-Good |
| 5,294,435 A | 3/1994 | Remz et al. |
| 5,342,536 A | 8/1994 | Miner et al. |
| 5,360,580 A | 11/1994 | Dotolo et al. |
| 5,486,305 A | 1/1996 | Faryniarz et al. |
| 5,866,104 A | 2/1999 | Cataneo et al. |
| 6,071,865 A | 6/2000 | Pickering et al. |
| 6,379,656 B2 | 4/2002 | Mui et al. |
| 6,521,572 B2 | 2/2003 | Perlman |

FOREIGN PATENT DOCUMENTS

EP    0009691    9/1979

*Primary Examiner*—Necholus Ogden
(74) *Attorney, Agent, or Firm*—Polster, Lieder Woodruff & Lucchesi, L.C.

(57) ABSTRACT

The present invention relates to a nail polish remover with excellent solvency and reduced environmental impact for use with artificial nails. Specifically, the nail polish remover contains methyl acetate, a glycol ether coupling agent, and a novel stabilizer. Further, the nail polish remover meets or exceeds contemporary regulations regarding air quality.

11 Claims, No Drawings

NAIL POLISH REMOVER

BACKGROUND OF THE INVENTION

The present invention relates to a nail polish remover with excellent solvency and reduced environmental impact. The remover of this invention is especially useful with artificial nails. Specifically, the nail polish remover contains methyl acetate, water, and a stabilizer. Further, the nail polish remover meets or exceeds contemporary regulations regarding air quality, while providing the same functional characteristics as products currently available.

Many compositions are known to be useful in removing nail polish. These compositions depend primarily on the activity of an organic solvent to soften or dissolve the nail polish. Subsequently, the polish is removed with a gentle rubbing motion. However, many of the existing compositions have shortcomings that preclude their use.

Growing concern about air quality has been driving national, state and local regulatory initiatives to improve air quality. Many of the products currently available will not be acceptable in the new regulatory environment. Ethyl acetate and ethanol have been employed as nail polish removing solvents for a long time and are currently used for artificial nail polish removal. Faryniarz describes an optimized system using ethyl acetate in U.S. Pat. No. 5,486,305. The combination is quite well suited to removing nail polish from artificial nails and has a history of safe use. However, both ethyl acetate and ethanol contribute to smog production and will no longer be environmentally acceptable in the State of California.

Nail polish removers currently available that exhibit acceptable environmental impact typically lack the aggressive solvency that consumers expect.

A thickened gamma butyrolactone (GBL) nail polish remover is described by Perlman in U.S. Pat. No. 6,521,572. GBL was the subject of an FDA Talk Paper in 1999 for its toxic effects. The potential for harm to consumers in the course of removing nail polish is too great to consider this material a viable option.

In U.S. Pat. No. 6,071,865, Pickering teaches a nail polish remover comprised of N-methylpyrrolidone (NMP) and fatty acid methyl or ethyl esters. Although the author claims low toxicity, NMP was listed under California Proposition 65 as a reproductive toxin in 2001.

A number of solvents have proven to have a limited impact on smog and have been exempted from governmental regulation. Acetone is the most notable exempted chemical for effective nail polish removal. Unfortunately, acetone is destructive to structured or artificial nail products. A number of other types of chemicals are also exempted, but tend to be too costly to be practical.

In U.S. Pat. No. 6,379,656, Mui describes a multi-phase nail polish remover with methyl acetate. A single phase system is not mentioned, nor is the system designed for low environmental impact.

In U.S. Pat. No. 5,866,104, Cataneo describes a nail polish remover with low volatility comprising glycol ethers and glycol ether esters. The more effective blends identified in the description do not currently meet regulatory requirements for VOC content, due to unacceptable vapor pressures and boiling points. The less effective blends do not offer the solvency required for an adequate nail polish remover.

The object of the current invention is to provide a safe, effective, and environmentally acceptable nail polish remover for artificial nails.

SUMMARY OF THE INVENTION

The invention comprises a single phase aqueous methyl acetate nail polish remover composition, which is environmentally acceptable and compatible with artificial nails.

DETAILED DESCRIPTION OF THE INVENTION

The following detailed description illustrates the invention by way of example and not by way of limitation. This description will clearly enable one skilled in the art to make and use the invention, and describes several embodiments, adaptations, variations, alternatives and uses of the invention, including what I presently believe is the best mode of carrying out the invention. As various changes could be made in the above constructions without departing from the scope of the invention, it is intended that all matter contained in the above description or shown in the accompanying drawings shall be interpreted as illustrative and not in a limiting sense.

The following examples are given to illustrate the composition of the present invention, but are not to be construed as limiting:

| Ingredients | Amount w/w % | Characteristics |
|---|---|---|
| Example No. 1 | | |
| Methyl Acetate (High Purity — Eastman Kodak) | 40 | The nail polish remover was clear. The composition was |
| Diethylene glycol monobutyl ether (Butyl Carbitol — Dow Chemical) | 16 | tested with a consumer panel for efficacy as compared to current |
| Dimethyl Esters (DBE-3, DuPont) Vapor Pressure <0.1 mm Hg at 20° C. | 5 | commercial products. Stability testing was executed and found |
| Sodium Acetate | 0.05 | that the hydrolytic stability of the |
| Purified Water | 38.75 | composition was adequate. |
| Fragrance | 0.2 | |
| Example No. 2 | | |
| Methyl Acetate (High Purity — Eastman Kodak) | 30 | The nail polish remover was slightly hazy. The composition |
| Diethylene glycol monobutyl ether (Butyl Carbitol — Dow Chemical) | 15 | was tested with a consumer panel for efficacy as compared to |
| Dimethyl Esters (DBE-3, DuPont) | 5 | current commercial products. |

| Ingredients | Amount w/w % | Characteristics |
| --- | --- | --- |
| Vapor Pressure <0.1 mm Hg at 20° C. | | Stability testing was executed |
| Sodium Acetate | 0.1 | and found that the hydrolytic |
| Purified Water | 49.7 | stability of the composition was |
| Fragrance | 0.2 | adequate. |
| Example No. 3 | | |
| Methyl Acetate | 25 | The nail polish remover was |
| (High Purity — Celanese) | | clear. The composition was |
| Diethylene glycol monobutyl ether | 8.8 | tested for solvency as compared |
| (Butyl Carbitol — Dow Chemical) | | to current commercial products. |
| Dimethyl Esters (DBE-3, DuPont) | 0.1 | The nail polish remover was |
| Vapor Pressure <0.1 mm Hg at 20° C. | | marginally successful. |
| Sodium Acetate | 0.1 | |
| Purified Water | 65.8 | |
| Fragrance | 0.2 | |
| Example No. 4 | | |
| Methyl Acetate | 20 | The remover was clear. When |
| (High Purity — Celanese) | | tested against commercial |
| Diethylene glycol monobutyl ether | 59.9 | products, the remover exhibits |
| (Butyl Carbitol — Dow Chemical) | | adequate solvency, but |
| Dimethyl Esters (DBE-3, DuPont) | 10 | evaporates more slowly than |
| Vapor Pressure <0.1 mm Hg at 20° C. | | commercial products. |
| Sodium Acetate | 0.1 | |
| Purified Water | 9.8 | |
| Fragrance | 0.2 | |
| Example No. 5 | | |
| Methyl Acetate | 30.51 | The remover was slightly hazy. |
| (High Purity — Eastman Kodak) | | The solvency was comparable to |
| Diethylene glycol monobutyl ether | 14.76 | commercial products. The |
| (Butyl Carbitol — Celanese) | | hydrolytic stability is comparable |
| Dimethyl Esters (DBE-3, DuPont) | 4.92 | to the sodium acetate |
| Vapor Pressure <0.1 mm Hg at 20° C. | | compositions. |
| Purified Water | 49.5 | |
| Fragrance | 0.2 | |
| Monobasic Portasium Phosphate | 0.04 | |
| Sodium Hydroxide to pH 7 | 0.01 | |
| Example No. 6 | | |
| Methyl Acetate | 30 | The remover was clear. When |
| (High Purity — Celanese) | | tested for solvency against |
| Acetone | 20 | commercial products, it was |
| Diethylene glycol monobutyl ether | 15 | comparable. When tested on |
| (Butyl Carbitol — Dow Chemical) | | artificial nails and nail glue, the |
| Dimethyl Esters (DBE-3, DuPont) | 5 | nail glue was not affected, but the |
| Vapor Pressure <0.1 mm Hg at 20° C. | | artificial nail softened |
| Fragrance | 0.2 | unacceptably. |
| Sodium Acetate | 0.1 | |
| Purified Water | 29.7 | |

The present invention uses an aqueous single phase methyl acetate solvent composition. The principal active ingredient is methyl acetate. The methyl acetate can be from about 20 to about 80% of the composition and preferably is about 30 to about 50%.

Optionally, a dimethyl ester with a vapor pressure less that 0.1 mm Hg at 20° C. can be used to increase the activity of the methyl acetate. The dimethyl ester is present in an amount of about 0.1 to about 10% and preferably from 3 to about 5%. The preferred dimethyl ester is a commercial product, DuPont DBE-3, which is a blend of dimethyl adipate and dimethyl glutarate and has a vapor pressure of less than 0.1 mm Hg at 20° C.

The methyl acetate has a solubility in water of 22%. To increase solubility and make a haze free single phase system, a glycol ether coupling agent is used in the amount of about 5% to about 75% and preferable from about 10% to about 20%. The glycol ether has a vapor pressure of less than 0.1 mm Hg at 20° C.

A buffering agent is included to reduce the rate of ester hydrolysis. The optimum pH is 5.0 to 9.0 with pH of about 7.0 as the preferred value. Sodium acetate is the preferred buffering agent in an amount of about 0.1% to about 10%; another possible buffer system is phosphate based.

Fragrance, dye, conditioning agents, emollients, and humectants can be included in the composition as desired, from 0 to 10%. Suitable humectants include glycerine, propylene glycol, fatty acid esters and mixtures thereof. Humectants can be included in the composition as desired.

Purified water in an amount of about 10 to about 70% is used to bring the composition to 100%. Preferably about 30 to about 50% purified water is used.

Acetone can be combined in an amount of about 0.1 to about 20%, preferably about 5%. However, acetone is destructive to structured nail products.

In view of the above, it will be seen that the several objects and advantages of the present invention have been achieved and other advantageous results have been obtained.

It is to be understood that the present invention is not limited to the exact description or examples given, and that various modifications and equivalents will be apparent to those skilled in the art.

Having thus described the invention, what is claimed and desired to be secured by Letters Patent is:

1. A single phase aqueous based nail polish remover composition comprising:
   a) about 20 to about 80% methyl acetate;
   b) about 5% to about 75% of a glycol ether coupling agent;
   c) an effective amount of a buffering agent to maintain a pH of about 5 to about 9; and
   d) about 10% to about 70% water.

2. The composition of claim 1 including about 0.1% to about 10% of a dimethyl ester with a vapor pressure of less than 0.1 mm Hg at 20° C.

3. The composition of claim 1 wherein the buffering agent is about 0.01% to about 1.0% sodium acetate.

4. The composition of claim 1 including about 0 to about 10% additives selected from the group consisting of dyes, conditioning agents, emollients, humectants and mixtures thereof.

5. The composition of claim 1 including about 1.0% to about 20% acetone.

6. The composition of claim 5 including about 5% acetone.

7. The composition of claim 1 wherein the pH is about 7.

8. The composition of claim 1 including a humectant for improving nail and skin conditioning.

9. The composition of claim 8 wherein the humectant is selected from the group consisting of glycerin, propylene glycol and fatty acid esters.

10. The composition of claim 1 wherein the glycol ether is diethylene glycol monobutyl ether.

11. The composition of claim 2 wherein the dimethyl ester is a blend of dimethyl adipate and dimethyl glutarate.

* * * * *

(12) INTER PARTES REEXAMINATION CERTIFICATE (1287th)
United States Patent
Holtz

(10) Number: US 6,841,523 C1
(45) Certificate Issued: Jun. 24, 2016

(54) NAIL POLISH REMOVER

(75) Inventor: Benjamin J. Holtz, St. Louis, MO (US)

(73) Assignee: VI-JON, INC., St. Louis, MO (US)

Reexamination Request:
No. 95/001,150, Apr. 14, 2009

Reexamination Certificate for:
Patent No.: 6,841,523
Issued: Jan. 11, 2005
Appl. No.: 10/670,407
Filed: Sep. 25, 2003

(51) Int. Cl.
*A61K 8/34* (2006.01)
*A61K 8/37* (2006.01)
(52) U.S. Cl.
CPC .... *A61K 8/34* (2013.01); *A61K 8/37* (2013.01)

(58) Field of Classification Search
USPC .......................................... 510/118
See application file for complete search history.

(56) References Cited

To view the complete listing of prior art documents cited during the proceeding for Reexamination Control Number 95/001,150, please refer to the USPTO's public Patent Application Information Retrieval (PAIR) system under the Display References tab.

*Primary Examiner* — Krisanne Jastrzab

(57) ABSTRACT

The present invention relates to a nail polish remover with excellent solvency and reduced environmental impact for use with artificial nails. Specifically, the nail polish remover contains methyl acetate, a glycol ether coupling agent, and a novel stabilizer. Further, the nail polish remover meets or exceeds contemporary regulations regarding air quality.

INTER PARTES REEXAMINATION CERTIFICATE

THE PATENT IS HEREBY AMENDED AS INDICATED BELOW.

AS A RESULT OF REEXAMINATION, IT HAS BEEN DETERMINED THAT:

Claims 1-11 are cancelled.

* * * * *